United States Patent
Famulok et al.

(10) Patent No.: US 9,910,045 B2
(45) Date of Patent: Mar. 6, 2018

(54) METHOD OF DETERMINING A PROTEIN IN A SAMPLE

(71) Applicant: RHEINISCHE FRIEDRICH-WILHELMS UNIVERSITAT BONN, Bonn (DE)

(72) Inventors: Michael Famulok, Bonn (DE); Gunter Mayer, Bonn (DE); Jan Vinkenborg, Eindhoven (NL)

(73) Assignee: RHEINISCHE FRIEDRICH-WILHELMS UNIVERSITAT BONN, Bonn (DE)

(*) Notice: Subject to any disclaimer, the term of this patent is extended or adjusted under 35 U.S.C. 154(b) by 0 days.

(21) Appl. No.: 15/258,962

(22) Filed: Sep. 7, 2016

(65) Prior Publication Data

US 2017/0059576 A1    Mar. 2, 2017

Related U.S. Application Data

(63) Continuation of application No. 14/416,450, filed as application No. PCT/EP2013/065690 on Jul. 25, 2013, now abandoned.

(30) Foreign Application Priority Data

Jul. 26, 2012 (EP) .................................. 12178091

(51) Int. Cl.
| | |
|---|---|
| *C12N 15/115* | (2010.01) |
| *G01N 33/68* | (2006.01) |
| *G01N 33/543* | (2006.01) |
| *G01N 33/58* | (2006.01) |
| *G01N 33/574* | (2006.01) |

(52) U.S. Cl.
CPC ....... *G01N 33/6803* (2013.01); *C12N 15/115* (2013.01); *G01N 33/54326* (2013.01); *G01N 33/57423* (2013.01); *G01N 33/585* (2013.01); *C12N 2310/16* (2013.01)

(58) Field of Classification Search
CPC ........................ C12N 15/115; G01N 33/57423
See application file for complete search history.

(56) References Cited

U.S. PATENT DOCUMENTS

| | | | |
|---|---|---|---|
| 8,440,801 B2 | 5/2013 | Nakamura et al. | |
| 2008/0293164 A1* | 11/2008 | Gaylord ............... | G01N 33/542 436/536 |
| 2009/0042206 A1* | 2/2009 | Schneider ............ | C12Q 1/6832 435/6.12 |

FOREIGN PATENT DOCUMENTS

| | | |
|---|---|---|
| EP | 2172566 | 4/2010 |
| EP | 2336314 | 6/2011 |
| WO | WO 2012004790 | 1/2012 |

OTHER PUBLICATIONS

Search Report and the Written Opinion of the International Searching Authority, PCT/EP2013/065690, dated Aug. 29, 2013.
Vinkenborg, et al.; "Aptamer-Based Affinity Labeling of Proteins". Angewandte Chemie, vol. 51, pp. 9176-9180, 2012.
Xihe Bi, et al.; "Affinity-Based Labeling of Cytohesins with a Bifunctional SecinH3 Photoaffinity Probe", Angewandte Chemie, vol. 47, pp. 9565-9568, 2008.

* cited by examiner

*Primary Examiner* — J. E. Angell
(74) *Attorney, Agent, or Firm* — Womble Bond Dickinson (US) LLP.

(57) ABSTRACT

The present invention relates to a method of determining a protein in a sample and the use of the method for the identification of aptamer target proteins.

11 Claims, 10 Drawing Sheets

METHOD OF DETERMINING A PROTEIN IN A SAMPLE

CROSS REFERENCE

This application is continuation of U.S. patent application Ser. No. 14/416,450, filed on Jan. 22, 2015, which is a U.S. National Phase Application under 35 U.S.C. § 371 of International Application No. PCT/EP2013/065690, filed on Jul. 25, 2013, which claims priority to EP12178091.0, filed on Jul. 26, 2012, the disclosures of which are all hereby incorporated by reference herein.

SEQUENCE LISTING SUBMITTED VIA EFS-WEB

The entire content of the following electronic submission of the sequence listing via the USPTO EFS-WEB server, as authorized and set forth in MPEP §1730 II.B.2(a), is incorporated herein by reference in its entirety for all purposes. The sequence listing is within the electronically filed text file that is identified as follows:
File Name: Sequence_Listing.txt
Date of Creation: Sep. 6, 2016
Size (bytes): 1,373 bytes

FIELD OF THE INVENTION

The present invention relates to methods of determining a protein in a sample. Particularly, the present invention relates to a method utilizing a functionalized aptamer.

BACKGROUND OF THE INVENTION

Aptamers are versatile, single stranded oligonucleotides that can be employed for the molecular recognition of different target structures via a strategy called Systematic Evolution of Ligands via EXponential enrichment (SELEX). Traditionally, aptamers were evolved against small molecules or proteins, and subsequently modified to enable application in a variety of in vitro assays. However, in recent years both the selection and application of aptamers has progressed towards considerably more complex targets such as cells, tissue slices or even live organisms. The target structures can be bound with high selectivity and affinity without knowledge of the actual molecule that is recognized by the aptamer. On the other hand, once an aptamer for targets of such complexity has been identified, this lack of knowledge immediately turns into a severe disadvantage, as it prevents further advancements, for example, as an analytical tool or as a biomarker for certain disease states. These restrictions require technologies that allow for the rational identification of unknown target molecules of an aptamer. Especially, the proteome-wide profiling or target identification of aptamers is not well established.

To identify aptamer targets photo-crosslinking of aptamers by photoreactive 5-iododeoxyuridines incorporated in an aptamer was used. However, the method suffers from a loss in affinity observed when introducing photoreactive nucleotides into an aptamer and requires tedious optimization of the position of the crosslinker moiety. Moreover, as this approach requires similar optimizations for other aptamer/target pairs, its general applicability is limited.

Therefore, the object underlying the present invention was to provide a method that allows for the identification of aptamer target structures. Especially it was an object of the present invention to provide a method that avoids optimization for each aptamer/target pair.

INCORPORATION BY REFERENCE

All publications, patents and patent applications mentioned in this specification are herein incorporated by reference to the same extent as if each individual publication, patent or patent application was specifically and individually indicated to be incorporated by reference.

SUMMARY OF THE INVENTION

The problem is solved by a method of determining a protein in a sample, comprising the steps of:
(a) Providing an aptamer, which is functionalized at the 5'-end with a labeling reagent comprising a photo-activatable crosslinking moiety, a labeling moiety, and a linker moiety connecting the labeling reagent to the 5'-end of the aptamer;
(b) Incubating a sample comprising an aptamer target protein with the functionalized aptamer of step (a);
(c) Irradiating the sample with ultraviolet light for cross-linking the aptamer via the photo-activatable crosslinking moiety to the protein; and
(d) Determining the protein via the labeling moiety.

BRIEF DESCRIPTION OF THE DRAWINGS

The figures which follow serve to illustrate the invention in more detail but do not constitute a limitation thereof.

FIGS. 2A-B show the binding of trCLN3 to the target protein c-Met.

FIGS. 3A-B show the binding of D17.4 to the target protein IgE.

FIGS. 4A-B show the binding of C10.35 to the target protein cytohesin-2.

FIGS. 5A-B show the photo-affinity labeling of c-Met on the surface of H1838 cells.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

The problem is solved by a method of determining a protein in a sample, comprising the steps (a) Providing an aptamer, which is functionalized at the 5'-end with a labeling reagent comprising a photo-activatable crosslinking moiety, a labeling moiety, and a linker moiety connecting the labeling reagent to the 5'-end of the aptamer;

(b) Incubating a sample comprising an aptamer target protein with the functionalized aptamer of step (a);

(c) Irradiating the sample with ultraviolet light for crosslinking the aptamer via the photo-activatable crosslinking moiety to the protein; and (d) Determining the protein via the labeling moiety.

The method allows for the rational identification of aptamer target structures within complex samples. The functionalization of the 5'-end makes the method easily applicable to the multitude of existing aptamers. Highly efficient and specific cross-linking of aptamer-protein pairs with large differences in secondary structure was achieved without loss in affinity. The method hence provides a general strategy usable for a variety of aptamer/target structures.

Advantageously, the loss in affinity commonly observed when introducing photoreactive nucleotides into an aptamer is prevented by attaching the crosslinking moiety at the 5'-end of the aptamer. It was observed that the binding affinity for the respective protein targets was not altered after 5'-modification with the labeling reagent. Surprisingly it was found that attaching the crosslinking moiety distant from the bound protein did not prevent efficient cross-linking.

Positioning of the labeling reagent at the 5'-end of the aptamer surprisingly places the crosslinking moiety sufficiently close to the protein target to enable efficient cross-linking, yet at the same time distant enough from the binding site to prevent a loss in affinity. Advantageously, the invention provides an efficient aptamer-based affinity labeling of proteins.

The crosslinking of a photo-activatable crosslinking moiety can be initiated by irradiation with ultraviolet light, which provides a reactive species that can covalently link the functionalized aptamer to the protein. This provides a second or cross-linking further to the affinity-based linking of the aptamer to its protein target. In preferred embodiments, the photo-activatable crosslinking moiety is selected from the group comprising aryl azides, diazirine derivatives such as 3-trifluoromethyl-3-phenyl-diazirine, benzophenone, and benzophenone derivatives.

Aryl azides are also called phenyl azides. Upon photolysis, aryl azides form short-lived nitrenes that react nonspecifically by initiating addition reactions with double bonds or insertion into C—H and N—H sites or undergo ring expansion and react with nucleophiles, especially amines. Using a photoreactive phenyl azide crosslinker a nonselective coupling to the target protein can be provided. Diazirines are a class of organic molecules comprising a carbon bound to two nitrogen atoms which are double-bonded to each other, forming a three-membered ring. Diazirines can easily and efficiently be activated with long-wave UV light of 330-370 nm. Upon photo-activation diazirines provide a carbene which can form covalent bonds through addition reactions with any amino acid side chain or peptide backbone at distances corresponding to the spacer arm lengths of the labeling reagent. Diazirines can provide a less reactive but more specific coupling. Preferred are 3-aryldiazirines, especially diazirine derivatives such as 3-trifluoromethyl-3-phenyl-diazirine (TPD).

The labeling moiety provides for the determination or detection of the protein. The labeling moiety can be a part of a specific binding pair. Such a labeling moiety can have the function of an anchor moiety. Specific binding pairs used conventionally in biological assays are for example biotin, which can bind with avidin/streptavidin, neutravidin, or an anti-biotin antibody. In preferred embodiments, the labeling moiety is selected from the group comprising biotin and desthiobiotin.

A linker moiety connects the labeling reagent to the 5'-end of the aptamer. The linker moiety can provide that the crosslinking moiety is sufficiently close to the protein target to enable an efficient cross-linking but is distant enough from the aptamer to prevent a loss in aptamer affinity to the protein. Further, a certain length of the linker moiety can be required when steric effects dictate a distance between the potential reaction sites for crosslinking.

In preferred embodiments, the linker moiety provides a spacer arm length of about 6 Å to 45 Å, preferably about 9 Å to 40 Å, more preferably about 12 Å to 30 Å, particularly about 20 Å to 30 Å, between the 5'-end of the aptamer and the crosslinking moiety. As used herein, the term "spacer arm length" refers to the molecular span i.e. the distance between the 5'-end of the aptamer and the crosslinking moiety, or between the crosslinking moiety and the labeling moiety. A single bond between carbon atoms has a length of about 1.5 Å. A spacer arm lengths of about 6 Å to 45 Å roughly corresponds to a chain length of about 4 to 30 carbon or hetero atoms. A shorter linker moiety might influence the aptamer affinity to the protein, while a longer linker moiety might reduce efficient cross-linking. The linker moiety can have incorporated hetero atoms, for example resulting from the binding reaction of the crosslinking moiety, to the labeling reagent, or the binding site of the labeling reagent to the aptamer.

The linker moiety can be provided by the labeling reagent, for example if the labeling reagent has a chain-like molecule part up to the crosslinking moiety, which provides a sufficient spacer arm length. Preferably, the linker moiety comprises a linker separate from the labeling reagent. The linker can be provided by an alkyl-chain, which preferably is a linear and/or unsaturated chain. The alkyl linker can be a linear saturated $C_2$-$C_{10}$ alkyl group, preferably a $C_4$-$C_8$ alkyl group, more preferably a $C_5$-$C_6$ alkyl group. Alkyl chains can be incorporated at the 5'-position of an aptamer via Phosphoramidite Synthesis of the aptamer sequence. The linker moiety alternatively can be provided by linear polyethylene glycol (PEG)-units. Preferred are PEG-units according to formula HO—(CH$_2$CH$_2$O)$_n$—H wherein n preferably is 1 to 5, particularly 2 to 3 or 4.

Preferably, the labeling moiety is placed at a certain distance to the crosslinking moiety. Preferably, the labeling reagent provides a spacer arm length of about 9 Å to 30 Å, preferably about 12 Å to 20 Å between the crosslinking moiety and the labeling moiety. A spacer arm length of about 9 Å preferably of about 12 Å to 20 Å or 12 Å to 30 Å can provide that the labeling moiety may not disturb the crosslinking when reacting with its binding partner.

In preferred embodiments, the labeling reagent is Sulfo-succinimidyl-2-[6-(biotinamido)-2-(p-azidobenzamido) hexanoamido]ethyl-1,3'-dithiopropionate (Sulfo-SBED). Sulfo-SBED is commercially available for example from Thermo Scientific. Sulfo-SBED is a trifunctional crosslinking reagent containing a biotin, a sulfonated N-hydroxysuccinimide (Sulfo-NHS) active ester and a photoactivatable aryl azide. The NHS ester can react with primary amine groups of the amino acids at the 5'-position of the aptamer that can be incorporated via Phosphoramidite Synthesis of the aptamer sequence, to form covalent amide bonds. It is preferred that the aptamer is functionalized at the 5'-end with Sulfo-SBED. An aptamer 5'-functionalized with Sulfo-SBED provides a phenyl azide moiety for cross-linking, which could be changed for other crosslinkers such as diazirine derivatives, and also contains a biotin residue that can be employed for determining the aptamer-protein conjugate. For example, the biotin residue can be employed for enriching the aptamer-protein conjugate by incubating with avidin or streptavidin beads. Hence, the method can be used for the enrichment of a target protein from complex mixtures.

The counter binding reagent for the labeling moiety can be fluorescence-labeled. A fluorescence-labeling, for example provided by fluorescence-labeled neutravidin, can provide a visualization of the crosslinked aptamer protein complex by light microscopy. Further, the counter binding reagent of the labeling moiety can be attached to an antibody or beads, particularly magnetic beads. Counter binding reagents of the labeling moiety attached to an antibody provide for a determination of the target protein via Western Blot analysis. Further, target proteins can be visualized using fluorescence-labeled second antibodies.

Streptavidin-coated beads can be added after the cross-linking. In preferred embodiments, the method comprises the step of incubating a biotin-labeled cross-linked aptamer-protein complex formed in step (c) by with avidin-, neutravidin-, or streptavidin-coated magnetic beads. Subsequent incubation with streptavidin-coated magnetic beads allows the purification of the crosslinked aptamer-protein complex. Particularly, a labeling of cells with magnetic beads also expands the repertoire of methods for magnetic cell sorting. Further, a labeling reagent containing a biotin residue can be employed for enriching the aptamer-protein conjugate by incubating with avidin or streptavidin beads.

Determining a target protein can correspond to identifying unknown target proteins, for example for proteome-wide profiling or target identification of aptamers, or determining the amount of a known or unknown target protein. Determining a target protein can also correspond to visualizing a target protein by light microscopy or Western blotting.

The incubation of an aptamer target protein with the functionalized aptamer serves for the affinity binding of the aptamer to the protein. Conditions for affinity binding widely depend on the nature of aptamer and protein, and temperature and time can vary. For example, samples can be incubated at 37° C. for 30 minutes. Irradiating the sample with ultraviolet light serves for the crosslinking of the aptamer via the photoactivatable crosslinking moiety to the target protein. Conditions for crosslinking widely depend on the crosslinking moiety, and temperature and time can vary. For example, samples can be illuminated at 365 nm for 10 minutes, preferably under cooling on ice.

The functionalized aptamer can provide an efficient aptamer-based labeling reagent for the respective aptamer target protein. The broad applicability of the aptamer-based affinity labeling of proteins was confirmed using different aptamer-protein pairs employing aptamers representing a diversity of motifs of secondary structures such as G-quadruplexes, hairpin-loops, or internal bulges, and using aptamer-protein pairs that vastly differ in the cellular environment in which their respective target primarily resides, namely at the cell surface, in the blood stream, and in the cytoplasm.

Suitable aptamers are for example C10.35 (SEQ ID NO: 1), D17.4 (SEQ ID NO: 3), and trCLN3 (SEQ ID NO: 5). These aptamers bind to the target proteins cytohesin-2, immunoglobulin E (IgE), and c-Met, respectively.

The method can be applied to a broad variety of aptamer/protein complexes. Advantageously, the ability to specifically and reliably cross-link targets in complex media allows for a wide diversity of samples of biological structures. Especially, the method is not limited to purified protein samples, but extendable to highly complex biological contexts such as cellular lysate or even directly at the membranes of living cells. Hence, the sample can be a protein sample of a cell, tissue or organism, a cellular lysate, or a tissue slice. A sample also can be a living cell, a cell organelle, or a membrane of living cells or cell organelles. Especially, a sample can be a membrane or surface of a cell or cell organelle such as exosomes or microsomes.

As used herein, the term "sample" refers to any material, which probably contains target proteins which can be determined, including any liquid or fluid sample or solid material, particularly a sample derived from a biological source. The term sample particularly refers to biological material, for example cells, cell organelles, or tissues, or extracts of any of the foregoing, biological fluids, biological molecules, or supernatants.

Advantageously, cross-linking of the functionalized aptamer to its target protein is possible in complex mixtures of different proteins. The method opens up the opportunity to be directly applied to cell surface proteins in the context of living cells.

In preferred embodiments, step (d) includes determining a protein in a cell, or in an exosome, or in a circulating microvesicle. In further preferred embodiments, step (d) includes determining a protein on the surface of a cell, or of an exosome, or of a circulating microvesicle.

As used herein, the term "exosome" refers to small vesicles secreted by a wide range of mammalian cell types. Exosomes can be released from a cell when multivesicular bodies fuse with the plasma membrane. The term "circulating microvesicles" refers to larger vesicular bodies, which are fragments of plasma membrane shed from almost all cell types. Circulating microvesicles are released by a number of cell types during cellular activation and apoptosis and supposedly play a role in intercellular communication. The identification of these vesicles has opened a new era in the understanding of cell signaling and the process of molecular communication between cells. Especially human body fluids can contain exosomes and circulating microvesicles.

The method can crosslink aptamers to their target structures in a light-dependent and highly specific manner. The aptamer-protein-complexes can be enriched in vitro, from a cellular lysate or from the surface of living cells. The method allows one to study aptamer interactions in a variety of biological contexts.

Advantageously, the method further provides for a proteome-wide profiling or target identification of aptamers. Another aspect of the invention relates to a use of the method for the identification of aptamer target proteins, particularly for the identification of aptamer target proteins in the proteome of cells, tissue or organisms. Especially, the method can be used for the identification of proteins of exosomes or circulating microvesicles.

The term "proteome" as used herein refers to the entire set of proteins expressed by a genome, cell, tissue or organism. More specifically, the term proteome refers to the set of expressed proteins in a given type of cells or an organism at a given time under defined conditions. The term "proteome" also is used to refer to the collection of proteins in certain sub-cellular biological systems. A cellular proteome is the collection of proteins found in a particular cell type under a particular set of environmental conditions.

The methods also can be useful for complexes between an aptamer and a known target, for example for target validation inside cells. In another embodiment, the method is usable for target validation inside cells.

The method further opens up the opportunity to be directly applied to cell surface proteins in the context of living cells. This augments the repertoire of the method for specific cell surface labeling. In a further embodiment, the method is usable for cell surface labeling, or the labeling of exosomes or circulating microvesicles.

The method can comprise the incubation of a biotin-labeled cross-linked aptamer-protein complex with avidin-, neutravidin-, or streptavidin-coated magnetic beads. The labeling of cells with magnetic beads also expands the repertoire of the method for magnetic cell sorting.

Another aspect of the invention relates to the use of the method including incubation of a biotin-labeled cross-linked aptamer-protein complex with avidin-, neutravidin-, or streptavidin-coated magnetic beads for magnetic cell sorting.

Figure 1A:
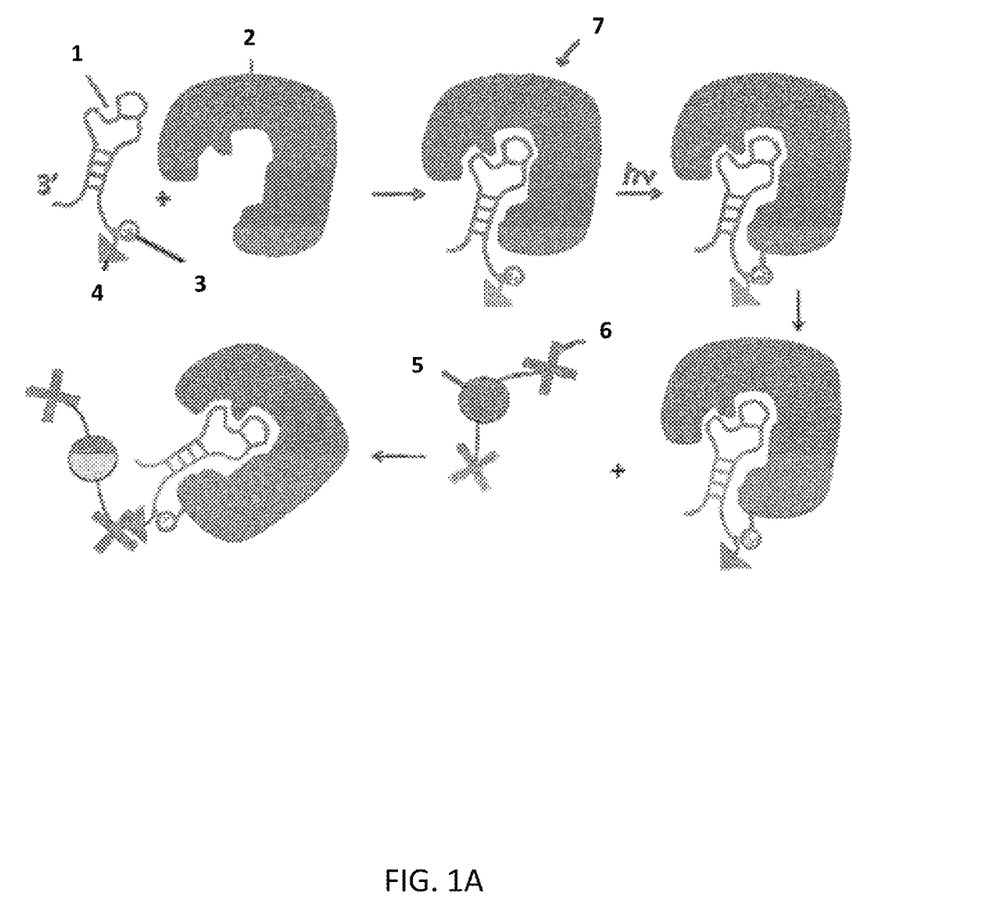
FIG. 1A shows a schematic representation of an embodiment of the method according to the invention.

FIG. 1A shows a schematic representation of an embodiment of the method of determining a protein in a sample. An aptamer 1 which is functionalized at the 5'-end with a labeling reagent containing a photo-activatable crosslinking moiety 3, which can be a phenyl azide, and a labeling moiety 4, which can be biotin, is incubated with a target protein 2. The aptamer 1 binds via affinity binding to the protein 2. In a next step the aptamer-protein complex 7 is irradiated with ultraviolet light (hv) for crosslinking the aptamer via the photoactivatable crosslinking moiety 3 to the protein 2. The protein can be determined by incubating the labeled cross-linked aptamer-protein complex 7 with magnetic beads 5 coated with a counter binding reagent 6, which can be streptavidin. Via binding of the labeling moiety 4 to the counter binding reagent 6 the aptamer-protein complex is attached to the beads. This allows for magnetic cell sorting.

Figure 1B:
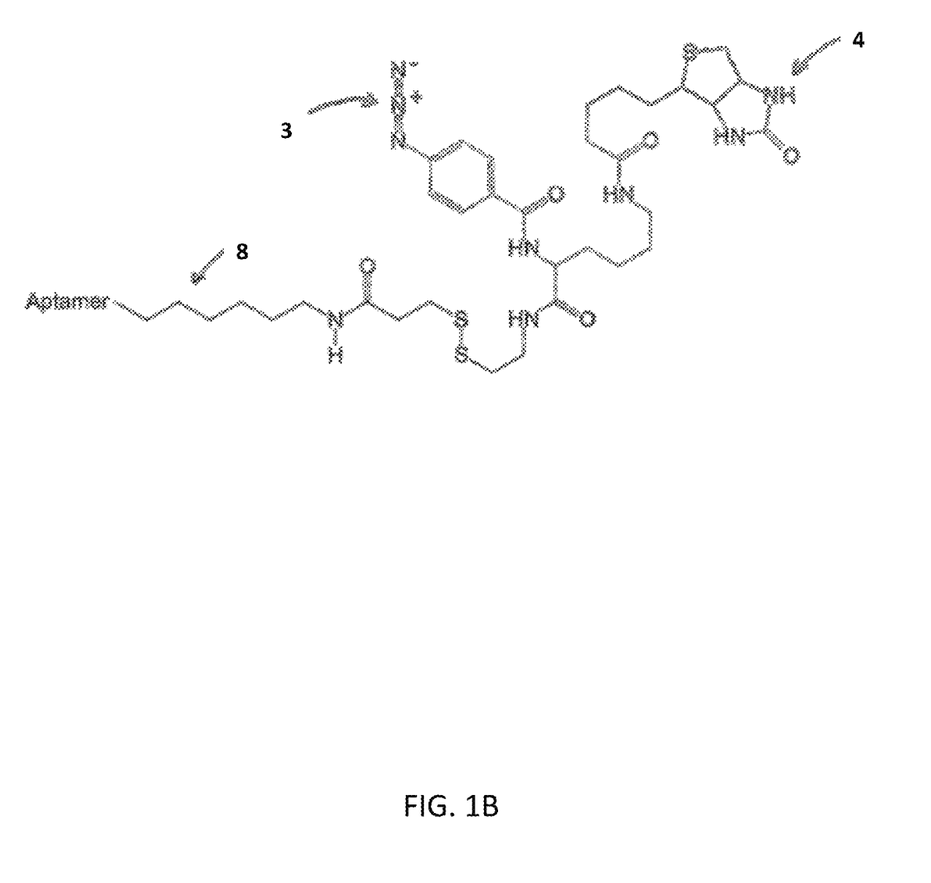
FIG. 1B shows the structure of an aptamer functionalized at the 5'-end with Sulfo-SBED, which is attached via a hexyl-group to the 5'-site of the aptamer.

FIG. 1B shows the structure of an aptamer functionalized at the 5'-end with Sulfo-SBED, which contains a phenyl azide 3 and a biotin 4, and which is attached via a hexyl-group linker 8 to the 5'-site of the aptamer.

Unless otherwise defined, the technical and scientific terms used herein have the same meaning as commonly understood by one of ordinary skill in the art to which this invention belongs.

The examples which follow serve to illustrate the invention in more detail but do not constitute a limitation thereof.

EXAMPLES

Materials and Methods

Aptamers according to Table 1, both unfunctionalized and functionalized with a hexylamine at the 5' site, were purchased in HPLC purified form from Metabion (Martinsried, Germany). The lyophilized samples were dissolved in double distilled H$_2$O (ddH$_2$O) to a concentration of 100 µM.

TABLE 1

Sequences of the individual aptamers

| Aptamer name | Sequence |
| --- | --- |
| C10.35/<br>SEQ ID NO: 1 | 5'-ACTCGGGAGGACTGCTTAGGATTGCGAACCCG<br>GGT-3' |
| C10.35 C15T/<br>SEQ ID NO: 2 | 5'-ACTCGGGAGGACTGTTTAGGATTGCGAACCCG<br>GGT-3' |
| D17.4/<br>SEQ ID NO: 3 | 5'-GGGGCACGTTTATCCGTCCCTCCTAGTGGCGT<br>GCCCC-3' |
| D17.4sc/<br>SEQ ID NO: 4 | 5'-CCAGCTGGCTCACCGTTCGCGCTAGGGCTTTC<br>CGTCG-3' |
| trCLN3/<br>SEQ ID NO: 5 | 5'-TGGATGGTAGCTCGGTCGGGGTGGGTGGGTTG<br>GCAAGTCT-3' |
| trCLN3 G25A/<br>SEQ ID NO: 6 | 5'-TGGATGGTAGCTCGGTCGGGGTGGATGGGTTG<br>GCAAGTCT-3' |

The Sec7 domain was expressed in *E. coli* and purified as described in X. Bi et al., Angew. Chem. 2008, 120, 9707-9710; Angew. Chem. Int. Ed. 2008, 47, 9565. IgE was purchased from Abcam (Cambridge, United Kingdom) and c-Met-Fc, which represents the ectodomain of c-Met fused to the Fe domain of human IgG$_1$ was bought at R&D Systems (Wiesbaden, Germany).

H1838 cells and HF460 cells were both cultured in RPMI 1640 (PAA, Colbe, Germany) supplemented with 10% fetal calf serum (Lonza, Verviers, Belgium).

Filter Retention Assays

Affinities and IC$_{50}$ values were determined using dot blot filter retention assays. First, aptamers C10.35, D17.4 and trCLN3 were radioactively labeled via addition of a $^{32}$P at the 5' site. A 20 µL solution containing 50 pmol aptamer, 6.7 pmol γ-$^{32}$P ATP and 20 U T4 Polynucleotide kinase (New England Biolabs, Frankfurt a. M., Germany) in 1× Polynucleotide buffer was incubated for 1 h at 37° C., followed by removal of unreacted γ-$^{32}$P ATP using an Illustra™ Microspin™ G-25 column (GE Healthcare, München, Germany). The purity of the radiolabeled aptamer was confirmed using a 10% PAGE-gel, which was also used to determine the percentage of radioactive signal caused by the aptamer.

To determine the affinity, ~10 fmol of radiolabeled aptamer was incubated with protein dilution series for 30 min at 37° C. in 25 µL of buffer containing 1 mg/ml *E. coli* tRNA (Roche, Mannheim, Germany), 1 µg/ml BSA, 3 mM MgCl$_2$ in PBS, pH 7.4. For Sec7, 0.005% Triton X-100 was added and for c-Met-Fc, 1 mg/ml of BSA was used instead of 1 µg/ml. The aptamer-protein complexes were captured on a Protran™ nitrocellulose membrane (GE Healthcare) that was pre-incubated in 0.4 M KOH for 10 minutes, followed by washing with ddH$_2$O and PBS containing 3 mM MgCl$_2$, pH 7.4. After addition of the aptamer-protein solution, the filter was washed 4 times with PBS containing 3 mM MgCl$_2$, pH 7.4. Radioactivity was quantified using a Fujifilm Fla-3000 PhosphorImager and AIDA software package. The percentage of bound aptamer was calculated using equation 1:

$$\% \text{ of bound aptamer} = \frac{cpm_{sample} - cpm_{background}}{(cpm_{total} - cpm_{background}) \cdot n} \cdot 100\% \quad (1)$$

in which $cpm_{sample}$ is an the radioactive signal of the sample of interest and $cpm_{background}$ the signal of the control sample without radioactive aptamer and n the correction factor for the amount of radioactive signal arising from the aptamer. $Cpm_{total}$ is the total radioactive signal, obtained from a dot blot of the radioactive aptamer solution on the nitrocellulose membrane without subsequent washing. The $K_d$'s were determined via equation (2) using Graphpadprism software, assuming a single binding event and no cooperativity in binding $$\% \text{ of bound aptamer} = a \cdot \frac{x}{x + K_d} + b \quad (2)$$

In (2), x is the protein concentration in mol·l$^{-1}$, $K_d$ is the binding affinity in M and a and b are constants that are included in the fit.

IC$_{50}$'s were obtained using a similar filter retention assays, yet in which ~10 fmol of aptamer was incubated with a protein concentration approximately 2-fold below the determined $K_d$ (75 nM for C10.35, 50 nM for IgE and 20 nM for c-Met-Fc), together with dilution series of either non-radioactive, unfunctionalized aptamer or the ABAL-functionalized variants of the aptamers. The percentage of the maximal radioactive signal was determined using equation (3), $$\% \text{ of maximum signal} = \frac{cpm_{sample} - cpm_{background}}{cpm_{max} - cpm_{background}} \cdot 100\% \quad (3)$$

in which $cpm_{sample}$ represents the radioactive signal of the respective sample, $cpm_{background}$ the signal in absence of radiolabeled aptamer and $cpm_{max}$ the signal obtained for a sample containing only protein and radiolabeled aptamer. The plots displaying the percentage of the maximum signal as a function of the amount of competing aptamer were fitted using equation (4) to obtain the IC$_{50}$, in mol·l$^{-1}$.

$$\% \text{ of maximum signal} = a + \frac{b - a}{1 + 10^{x - \log(EC_{50})}} \quad (4)$$

In equation (4), x is the amount of competing aptamer in mol·l$^{-1}$ and a and b are constants that are included in the fit and represent the minimum and maximum percentage, respectively.

Example 1: Generation of the Functionalized Aptamers

Sulfo-N-hydroxysuccinimidyl-2-(6-[biotinamido]-2-(p-azido benzamido)-hexanoamido) ethyl-1,3'-dithioproprionate (Sulfo-SBED; Thermo Scientific, USA) was freshly dissolved in dry DMSO to a concentration of 20 mM. Coupling was performed in brown Eppendorf tubes with a 100-fold excess of sulfo-SBED in a buffer consisting of 25 mM Hepes, 100 mM NaCl, 20% dry DMSO and 40 μM of the respective aptamer.

Purification of the functionalized aptamers was performed on an Agilent 1100 series HPLC (Agilent, Boblingen, Germany) using a C18 Zorbax SB-Aq column (4.6×150 mm; Agilent) by applying a gradient of 0.1 M tetraethylammoniumacetate (TEAAc) up to 25% acetonitrile. The fraction containing the functionalized aptamer was dried overnight using a Concentrator 5301 (Eppendorf, Gern1any) at 4° C. and the resulting solid was dissolved in ddH$_2$O, aliquoted and stored at a concentration of 30-40 μM at −20° C. in brown eppendorf tubes.

Example 2: In Vitro Cross-Linking of the 5'-Functionalized Aptamer trCLN3 with c-Met Determined was the cross-linking of the DNA aptamer CLN0003, hereafter referred to as CLN3, which recognizes the ectodomain of the membrane protein hepatocyte growth factor receptor (HGFR) also known as c-Met. According to the analysis of the inventors, this aptamer has two G-quadruplex structures. Used was a commercially available fusion protein between the ectodomain of c-Met and an IgG Fe domain (c-Met-Fc).

A variant of the DNA aptamer CLN3 that was truncated to 40 nucleotides and hereafter is referred to as trCLN3 (SEQ ID NO: 5) that binds c-Met with nanomolar affinity was functionalized at its 5'-end with Sulfo-SBED as labeling reagent as described in Example 1. The resulting functionalized aptamer was separated from the excess unreacted Sulfo-SBED and unreacted trCLN3 aptamer by reverse phase HPLC.

Incubating the target protein c-Met with the 5'-functionalized aptamer trCLN3 was performed by mixing 250 nM of the aptamer with different protein concentrations in a round-bottom polypropylene 96 wells plate (Brand, Wertheim, Germany) using the buffer from the filter binding experiments. Samples were covered from light using aluminium foil and incubated at 37° C. for 30 min. Subsequently, control samples without UV light were stored in the dark at 4° C., whereas crosslinking was performed by placing the 96-wells plate containing the remaining samples on ice and illuminating at 365 nm for 10 minutes using a UVP 3UV lamp (Thermo Scientific, Rockford, USA).

To test the influence of the 5'-functionalisation on aptamer binding filter retention assays as described above were performed in which the 5'-functionalized aptamer competed with non-derivatized aptamer for binding to c-Met.

Figure 2A:
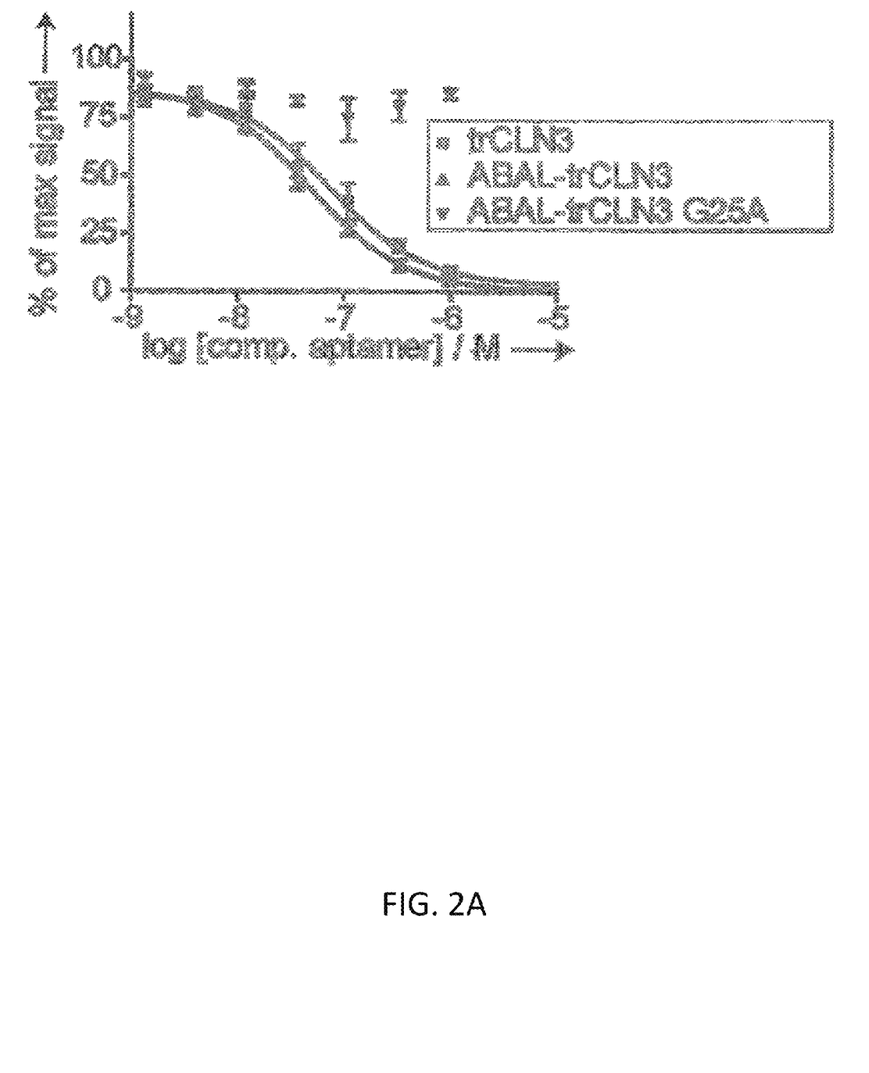
FIG. 2A shows the result of the filter retention assay in which increasing concentrations of 5'-functionalized variants of trCLN3 competed with radiolabeled trCLN3 for binding to the target protein c-Met.

FIG. 2A shows that the IC$_{50}$ of 5'-functionalized aptamer trCLN3 (ABAL-trCNN3) was 50±8 nM, which is similar to the 76±17 nM obtained for the unlabeled trCLN3. This result demonstrates that functionalization of the 5' site of the aptamer did not affect its binding affinity. FIG. 2A also shows that a 5'-functionalized non-binding G25A point-mutant of trCLN3 (ABAL-trCLN3 G25A, SEQ ID NO: 6) displayed no binding in the tested concentration range. This result established a negative-control and confirmed that no non-specific cross-linking occurred without affinity-binding via the aptamer in the incubation step. This also confirmed the G-quadruplex structure of the aptamer.

Further, the amount of cross-linking of the 5'-functionalized aptamer trCLN3 to purified c-Met was investigated. c-Met was incubated in concentrations of 0.5 µM, 167 nm, 56 nm and 19 nM with 250 nM of the 5'-functionalized aptamer trCLN3 and trCLN3 G25A, followed by UV irradiation at 365 nm. The amount of cross-linking was analyzed using SDS-PAGE, followed by western blotting using fluorescence-labeled neutravidin-Dylight™ 800 (Thermo Scientific) to visualize biotinylated proteins. Anti-penta-his (1:2000, Qiagen) was used to visualize the total amount of c-Met-Fc. Goat-anti-mouse-IgG-Dylight™ 800 (Thermo Scientific) was used as a secondary antibody. The blots were scanned at 800 nm using an Odyssey scanner (Li-cor Biotechnology, Bad Homburg, Germany).

Figure 2B:
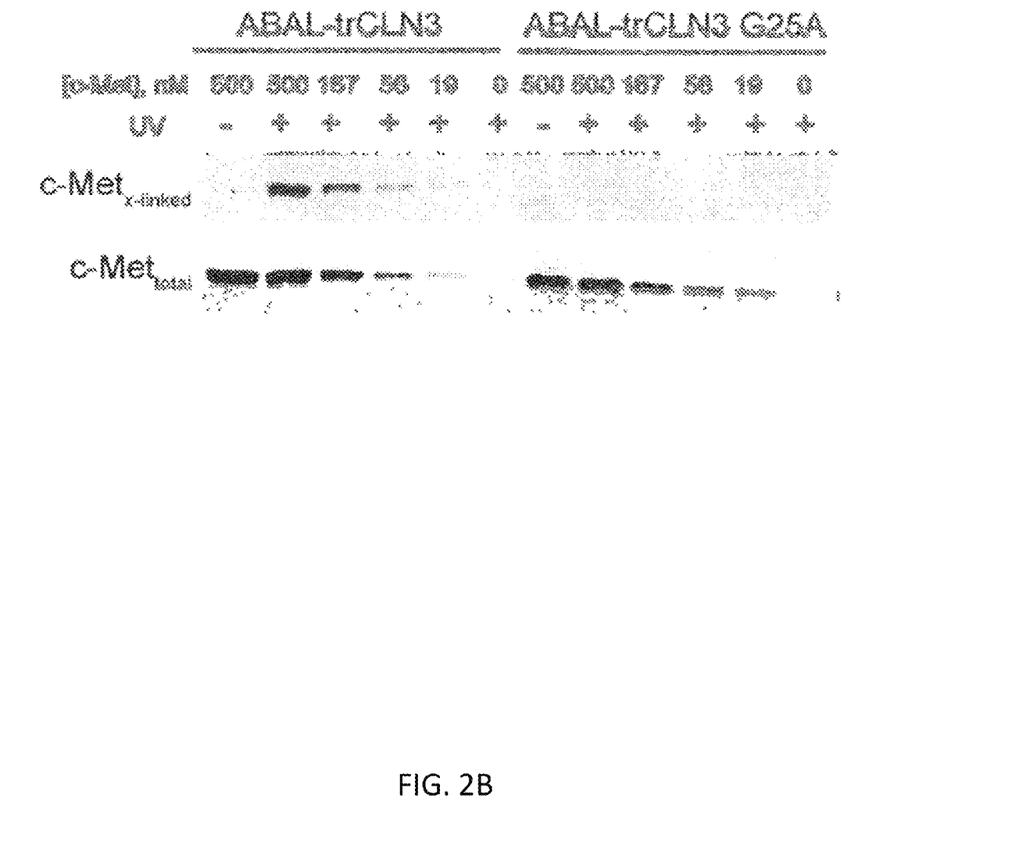
FIG. 2B shows the Western blot analysis of cross-linking between 5'-functionalized trCLN3 (ABAL-t:rCLN3) and c-Met (left panel) as compared to a non-binding point mutant of the aptamer trCLN3 (right panel).

FIG. 2B shows that no cross-linking occurred in the absence of UV irradiation. But after exposure to 365 nm light, a high level of cross-linking was observed between 5'-functionalized trCLN3 and 0.5 µM c-Met. Even at concentrations as low as 19 nM of c-Met cross-linking was still clearly detectable. In contrast, even the highest concentration of c-Met resulted in very low cross-linking when 5'-functionalized trCLN3 G25A was used; quantification of the band intensities at 500 nM c-Met revealed a 24-fold lower signal as compared to 5'-functionalized trCLN3.

This difference clearly shows that the reaction strictly depends on the affinity binding of the aptamer combined with crosslinking via UV-irradiation.

Example 3: Determination of the Cross-Linking Efficiencies of the 5'-Functionalized Aptamer Tr•CLN3 with c-Met In Vitro Cross-linking efficiencies were determined by cross-linking 250 nM of the 5'-functionalized aptamer trCLN3 with 0.5 µM of c-Met-Fc as described above, followed by addition of 30 µg MyOne™ streptavidin Dynabeads (Invitrogen) to 50 µL of cross-linking sample and transfer into a brown eppendorf tube. This mixture was mixed overnight at 4° C. using a tumble shaker, after which a magnetic rack was used to collect the supernatant and wash the beads 3 times with 2 M NaCl, 1 mM EDTA, 0.01% Triton X-100 and 10 mM Tris-HCl, pH 7.5. The beads were then resuspended in 50 µL PBS. The supernatant, bead fraction and a dilution series of purified sec7 were analyzed via Western blots involving anti-penta-his (1:2000, Qiagen) in combination with anti-mouse-IgG-Dylight™ 800 (1:20000, Thermo Scientific). The band intensities were quantified using Quantity One™ software (Bio-rad). A dilution series of c-Met showed a linear correlation between protein concentration and band intensity and was used to generate a calibration curve. The quantified amount of cross-linked protein in the bead fraction was calculated and converted to the amount of cross-linked aptamer. This value was then divided by the total amount of aptamer to obtain the cross-link efficiency.

A comparison of the total amount of c-Met and the cross-linked c-Met fraction after UV irradiation revealed a cross-linking efficiency of approximately 30%. This efficiency is higher than the 5-20% efficiencies typically observed when using aptamers functionalized with 5-bromo- or 5-iododeoxyuridine residues, and similar to the efficiency observed with mRNA 2,4-dinitro-5-fluoro phenyl azide.

Thus, the observed high levels of functionalization demonstrate that positioning of the labeling reagent at the 5'-end of the aptamer places the phenyl azide sufficiently close to the protein target to enable efficient cross-linking, yet at the same time distant enough from the binding site to prevent a loss in affinity.

Example 4: In Vitro Cross-Linking of the 5'-Functionalized Aptamer D17.4 with Immunoglobulin E To estimate its generality of the method in vitro cross-linking of a 5'-functionalized aptamer was repeated using another aptamer/protein pair using the immunoglobulin E (IgE) binding DNA aptamer D17.4 (SEQ ID NO: 3), whose target primarily resides in the blood stream. The secondary structure of the aptamer D17.4 forms a simple hairpin-loop structure and differs from the secondary structure of the aptamer CLN3. For a non-binding variant to be used as negative control, a scrambled sequence variant D17.4sc (SEQ ID NO: 4) was created. Functionalization at the 5'-ends of aptamers D17.4 and D17.4sc with Sulfo-SBED as labeling reagent was performed as described in Example 1.

As described in Example 2, incubation of the target protein IgE with the 5'-functionalized aptamer D17.4 was performed by mixing 250 nM of the aptamer with different protein concentrations in a round-bottom polypropylene 96 wells plate (Brand, Wertheim, Germany) using the buffer from the filter binding experiments. Samples were covered from light using aluminum foil and incubated at 37° C. for 30 min. Subsequently, control samples without UV light were stored in the dark at 4° C., whereas crosslinking was performed by placing the 96-wells plate containing the remaining samples on ice and illuminating at 365 nm for 10 minutes using a UVP 3UV lamp (Thermo Scientific, Rockford, USA).

Figure 3A:
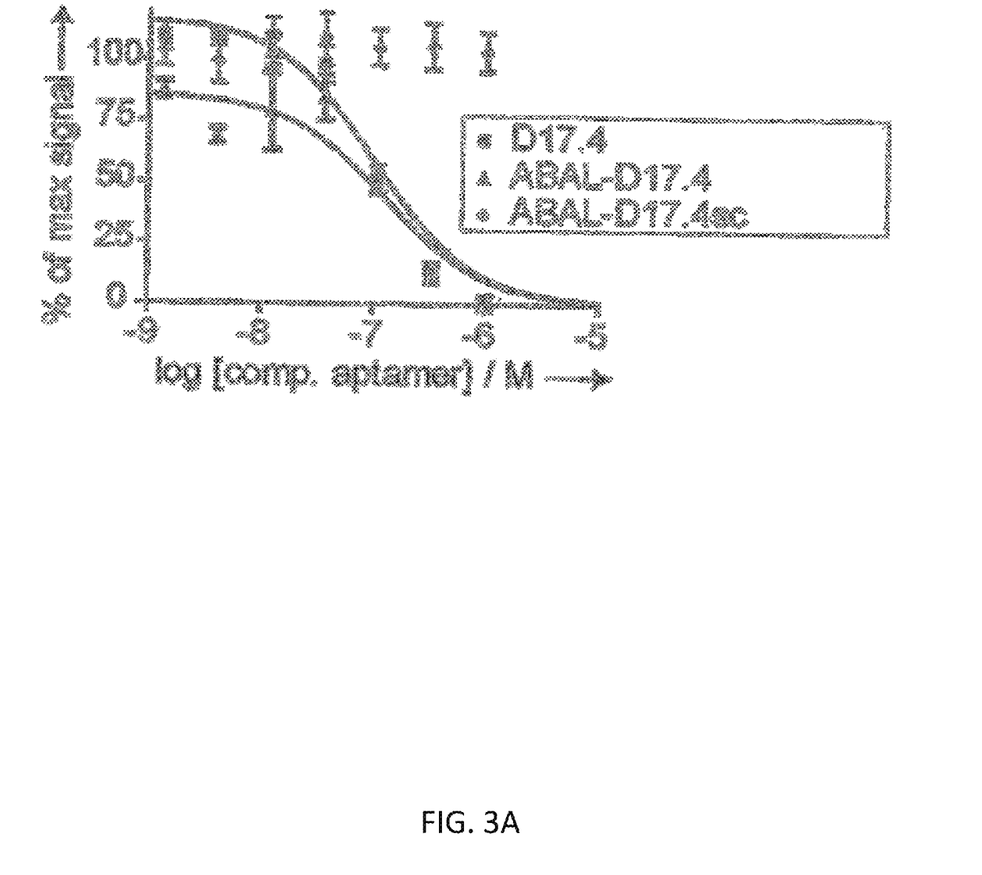
FIG. 3A shows the result of the filter retention assay in which increasing concentrations of 5'-functionalized variants of D17.4 competed with radiolabeled D17.4 for binding to the target protein IgE.

Filter retention assays in which the 5'-functionalized aptamer competed with the non-functionalized aptamer for binding to IgE were performed as described above to test the influence of the 5'-functionalization on aptamer binding. FIG. 3A shows that the binding affinity for the protein target IgE was not altered for the aptamer functionalized at the 5'-end with Sulfo-SBED (ABAL-D17.4) compared to the non functionalized aptamer (D17.4).

Figure 3B:
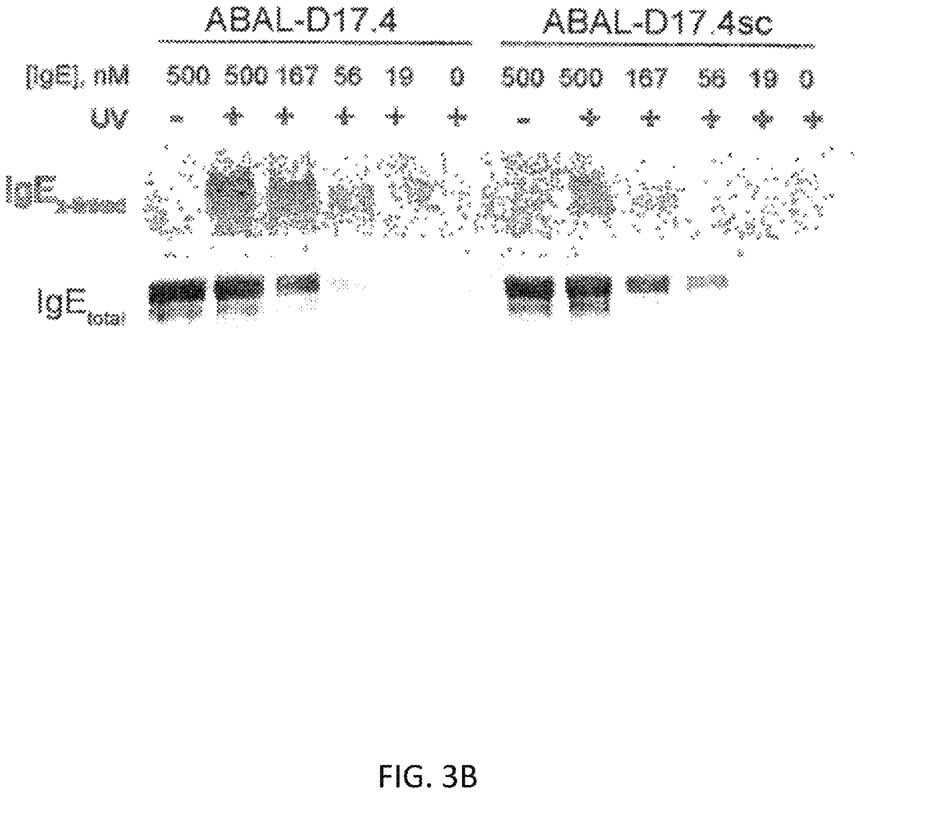
FIG. 3B shows the Western blot analysis of cross-linking between 5'-functionalized D17.4 (ABAL-D17.4) and IgE (left panel) as compared to a non-binding scrambled sequence of the aptamer D17.4 (right panel).

Further, the amount of cross-linking of the 5'-functionalized aptamer D17.4 to IgE was investigated. IgE was incubated in concentrations of 0.5 µM, 167 nm, 56 nm and 19 nM with 250 nM of the 5'-functionalized aptamer D17.4 and D17.4sc, followed by UV irradiation at 365 nm. The amount of cross-linking was analyzed using SDS-PAGE, followed by Western blotting using neutravidin-Dylight™ 800 (Thermo Scientific) to visualize biotinylated proteins. Anti-IgE (XTE4, mouse monoclonal, 1:500, Abcam) was used to visualize the total amount of IgE. The blots were scanned at 800 nm using an Odyssey scanner (Li-cor Biotechnology, Bad Homburg, Germany). FIG. 3B shows that high levels of cross-linking were observed for the 5'-functionalized aptamer D17.4 (ABAL-D17.4), whereas for the functionalized non-binding aptamer variant (ABAL-D17.4sc) marginal cross-linking was detectable at only the highest protein concentrations. Quantification of the cross-linking bands at the highest protein concentrations yielded differences in cross-linking of 17-fold between D17.4 and its negative control for IgE. This result is similar to the observation for 5'-functionalized aptamer trCLN3 in Example 2, indicating that the method can potentially be applied to a broad variety of aptamer/protein complexes.

Example 5: In Vitro Cross-Linking of the 5'-Functionalized Aptamer C10.35 with the Sec7 Domain of the Guanine Nucleotide Exchange Factor Cytohesin-2

In vitro cross-linking of a 5'-functionalized aptamer was repeated using the aptamer C10.35 (SEQ ID NO: 1) which binds the Sec7 domain of the guanine nucleotide exchange factor cytohesin-2 (Sec-7), a cytoplasmic protein required for activating small GTPases and receptor tyrosin kinases, respectively. The secondary structure of the aptamer C10.35 comprises a stem with a double bulge. For a non-binding variant to be used as negative control the non-binding point mutant C10.35 C15T (SEQ ID NO: 2) was used. Functionalization at the 5'-ends of aptamers C10.35 and C10.35 C15T with Sulfo-SBED as labeling reagent was performed as described in Example 1.

Incubation of the target protein Sec7 with the 5'-functionalized aptamer C10.35 was performed by mixing 250 nM of the aptamer with different protein concentrations at 37° C. for 30 min as described in Examples 2 and 4. Crosslinking also was performed on ice by illuminating at 365 nm for 10 minutes.

Figure 4A:
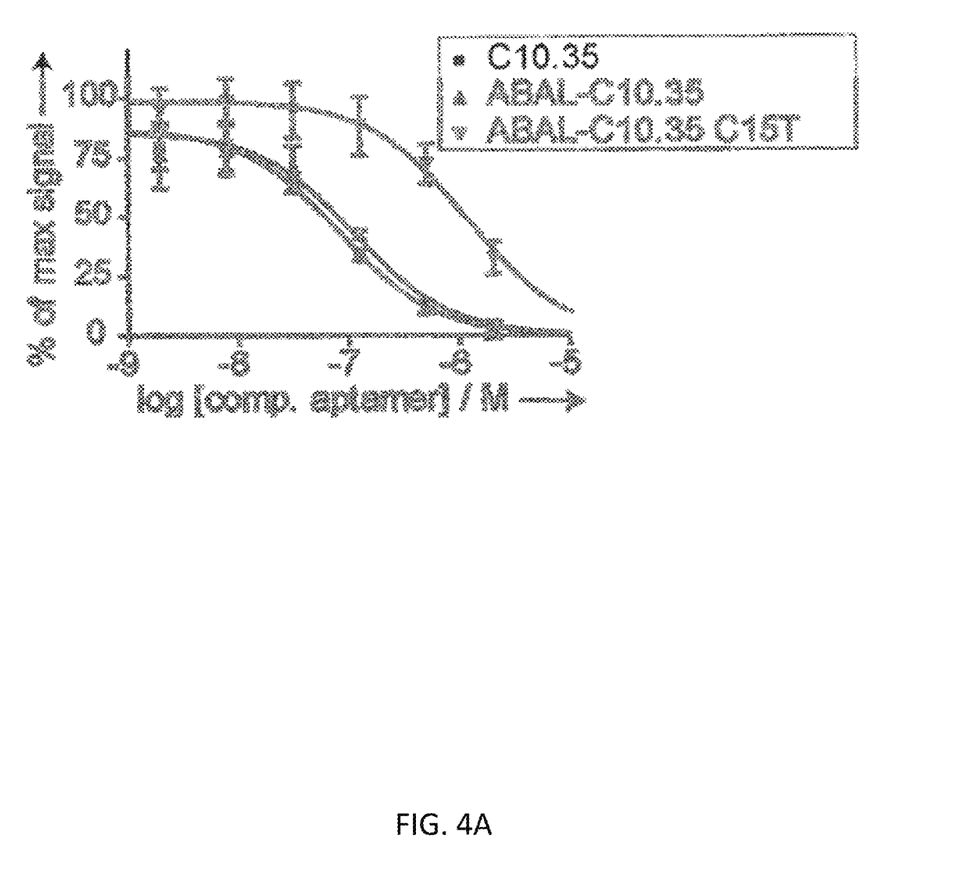
FIG. 4A shows the result of the filter retention assay in which increasing concentrations of 5'-functionalized variants of C10.35 competed with radio-labeled C10.35 for binding to the target protein cytohesin-2.

Filter retention assays in which the 5'-functionalized aptamer competed with the non-functionalized aptamer for binding to Sec-7 were performed as described above to test the influence of the 5'-functionalization on aptamer binding. FIG. 4A shows that the binding affinity for the protein target Sec-7 was not altered for the aptamer functionalized at the 5'-end with Sulfo-SBED (ABAL-C10.35) compared to the non functionalized aptamer (C10.35).

Further, the amount of cross-linking of the 5'-functionalized aptamer C10.35 to Sec-7 was investigated after incubating 0.5 μm 167 nm, 56 nm and 19 nM Sec-7 with 250 nM of the 5'-functionalized aptamers C10.35 and C10.35 C15T, followed by UV irradiation at 365 nm using SDS-PAGE, followed by western blotting using neutravidin-Dylight™ 800 (Thermo Scientific) to visualize biotinylated proteins. Anti-penta-his (1:2000, Qiagen) was used to visualize the total amount of Sec7 and goat-anti-mouse-IgG-Dylight™ 800 (Thermo Scientific) was used as a secondary antibody. The blots were scanned at 800 nm using an Odyssey scanner (Li-cor Biotechnology, Bad Homburg, Germany).

Figure 4B:
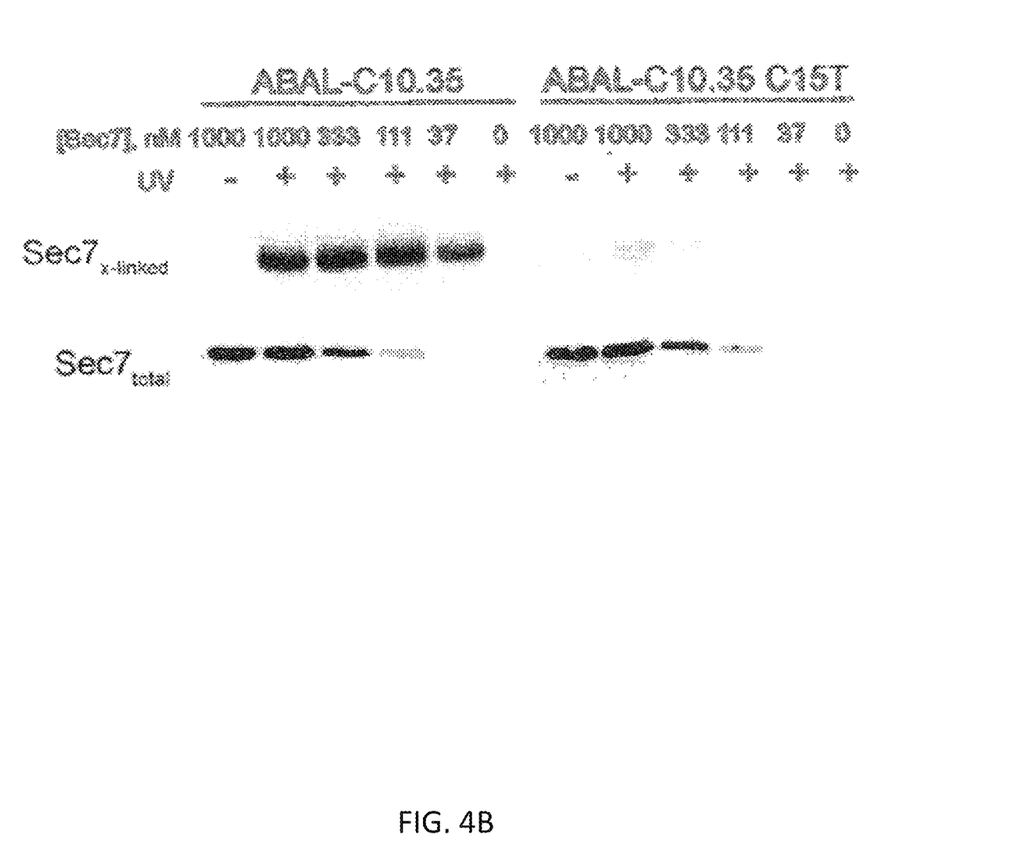
FIG. 4B shows the Western blot analysis of cross-linking between 5'-functionalized C10.35 (ABAL-C10.35) and cytohesin-2 (left panel) as compared to a non-binding point mutant of the aptamer C10.35 (right panel).

FIG. 4B shows that high levels of cross-linking were observed for the 5'-functionalized aptamer C10.35 (ABAL-C10.35), whereas for the functionalized non-binding aptamer variant (ABAL-C10.35 C15T) marginal cross-linking was detectable at only the highest protein concentrations. Quantification of the cross-linking bands at the highest protein concentrations yielded differences in cross-linking of 7-fold between C10.35 and its negative control for Sec-7. This result confirms that the method can potentially be applied to a broad variety of aptamer/protein complexes.

Example 6: Cross-Linking of a 5'-Functionalized Aptamer in a Cell Lysate

The ability to specifically and reliably cross-link targets in complex media was determined in a lysate from human H460 cells.

To a cell lysate of H460 cells of a final concentration of 2 mg/ml 250 nM of the 5'-functionalized aptamer C10.35 and 1 μM of Sec7 were added. As a control sample 1 μM of Sec7 and 250 nM of the 5'-functionalized negative control aptamer C10.35 C15T were added to respective lysate samples. Samples were covered from light using aluminium foil and incubated at 37° C. for 30 min. Subsequently, the samples were placed on ice and illuminated at 365 nm for 10 minutes using a UVP 3UV lamp (Thermo Scientific, Rockford, USA).

For visualization of crosslinked products SDS-PAGE, followed by western blotting using fluorescence-labeled neutravidin-Dylight™ 800 (Thermo Scientific) to visualize biotinylated proteins was used. Anti-penta-his (1:2000, Qiagen) was used to visualize the total amount of Sec7 and goat-anti-mouse-IgG-Dylight™ 800 (Thermo Scientific) was used as a secondary antibody. The blots were scanned at 800 nm using an Odyssey scanner (Li-cor Biotechnology, Bad Homburg, Germany).

A band corresponding to the molecular weight of Sec7 in the lysate was detected, whereas this band was absent when the negative control ABAL-C10.35 C15T was used. This demonstrates that cross-linking of the 5'-functionalized aptamer to its target protein is possible in complex mixtures of different proteins.

Example 7: Identification of Aptamer Target Proteins on the Cell Surface

H1838 cells, a non-small-cell lung carcinoma (NSCLC) cell line which is known to overexpress c-Met, were grown in a Ibidi μ-Dish 35 mm, low (Ibidi), and washed twice with PBS prior to addition of PBS containing 250 nM of 5'-functionalized trCLN3 aptamer and 1 mg/mL tRNA solution, pH 7.4. Control cells were incubated with the 5'-functionalized non-binding G25A point-mutant of trCLN3 or no aptamer. The cell samples were incubated for 30 minutes at 37° C. on a tilting platform, followed by 10 minutes of irradiation at 365 nm on ice. After addition of streptavidin-coated magnetic MyOne™ streptavidin Dynabeads (Invitrogen) to a final concentration of 0.25 mg/mL, the cells were incubated for 1 h at room temperature, washed 1× with PBS and subsequently used for microscopy imaging. Microscopy images where obtained using an Axio Observer.D1 microscopy (Zeiss) equipped with a Zeiss CD-plan Neofluar 40× objective and a PCO Sensicam detector.

Figure 5A:
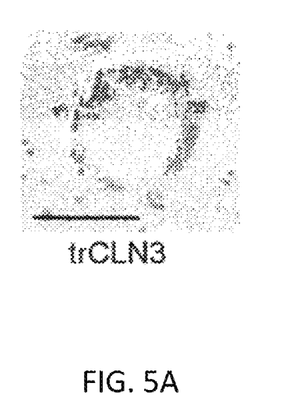
FIG. 5A shows light microscopy images of magnetic bead binding to H1838 cells incubated with 5'-functionalized trCLN3 (ABAL-trCLN3), FIG. 5B a 5'-functionalized non-binding G25A point-mutant of trCLN3 (ABAL-t:rCLN3 G25A), and FIG. 5C no aptamer. The scale bars indicate 25 µm.
Figure 5B:
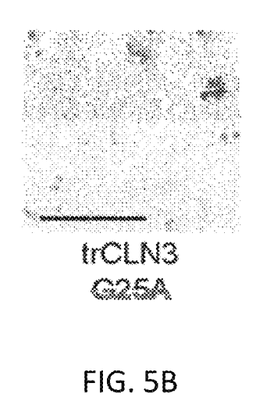
Figure 5C:
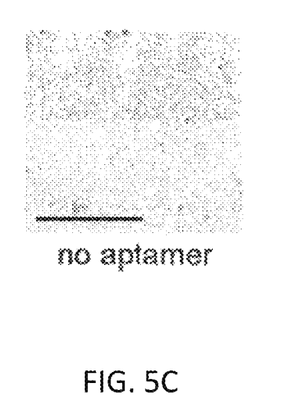

FIG. 5A shows the images of magnetic bead binding to H1838 cells incubated with 5'-functionalized trCLN3 (ABAL-trCLN3), FIG. 5B the 5'-functionalized non-binding mutant (ABAL-trCLN3 G25A), and FIG. 5C no aptamer. As is evident from FIG. 5A, cells incubated with the 5'-functionalized trCLN3 aptamer ABAL-trCLN3 showed impressively enhanced bead binding to their surface. Virtually no bead binding was observed when using the 5'-functionalized non-binding mutant, or no aptamer, as can be taken from FIGS. 5B and 5C respectively.

This result not only demonstrates that the identification of aptamer target proteins can be employed to targets in the context of living cells, but also shows that the specificity of the method observed in vitro is maintained. Furthermore, the efficient labeling of cells with magnetic beads also expands the repertoire of methods for magnetic cell sorting, which so far was restricted to the introduction of magnetism by antibodies.

Example 8: Enrichment of Target Protein in a Sample

H1838 cells were grown to 70-80%, followed by resuspension using Alfazyme (PAA, Cölbe, Germany). After Alfazyme treatment, the cells were centrifuged for 5 minutes at 200 g, resuspended in PBS and centrifuged again at 200 g for 5 minutes. For each sample ~8×10$^5$ cells were used and resuspended in PBS containing 1 mM $MgCl_2$ and 1 mg/ml tRNA, pH 7.4, together with 5'-functionalized trCLN3 aptamer, the 5'-functionalized non-binding G25A point-mutant of trCLN3 or no aptamer. Cells were incubated for 30 min at 37° C. in a tumble shaker followed by placement on ice and exposure to UV light of 365 nm for 10 minutes.

After cross-linking, the sample was transferred to a brown eppendorf tube containing 30 μg MyOne™ streptavidin Dynabeads (Invitrogen) and incubated in a tumble shaker for 1 hour at room temperature. Next, lysis buffer was added to a final concentration of 50 mM Tris, 10 mM MgCl$_2$, 200 mM NaCl, 5% glycerol, 1% Triton X-100, 1 mM PMSF, pH 7.4, and 1× protease inhibitor cocktail (Roche) and placed on ice for 20 min. Using a magnetic rack, the supernatant was separated from the beads, followed by 2 washes using 2 M NaCl, 1 mM EDTA, 1% Triton X-100 and 10 mM Tris-HCl, pH 7.5 and 1 wash using the same buffer except for 0.01% instead of 1% Triton X-100. The beads were resuspended in PBS, after which the supernatant and bead fraction were used for Western Blot analysis. Neutravidin-Dylight™ 800 (1:20000; Thermo Scientific) was used to visualize biotinylated proteins, whereas Met (C-28) antibody (SC-161, Santa Cruz Biotechnology, Santa Cruz, USA) was used in combination with fluorescence-labeled goat-anti-rabbit-IgG-Dylight™ 800 (1:20000; Thermo Scientific) for c-Met.

Figure 6:
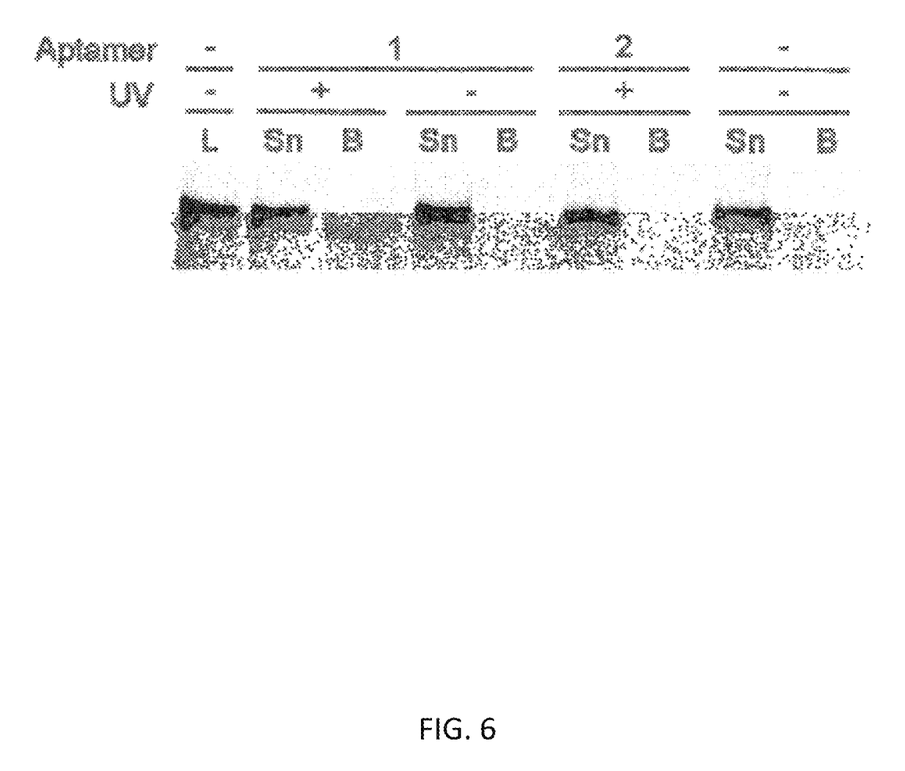
FIG. 6 shows Western Blot analysis of the supernatant (Sn) or bead (B) fractions of samples treated with 5'-functionalized trCLN3 (ABAL-trCLN3) (1), 5'-functionalized non-binding G25A point-mutant of trCLN3 (ABAL-trCLN3 G25A) (2) or no aptamer (−) in presence or absence of UV irradiation. Sample L contains H1838 cell lysate without aptamer.

FIG. 6 shows the Western Blot analysis of the supernatant (Sn) or bead (B) fractions of samples treated with 5'-functionalized trCLN3 (ABAL-trCLN3) (1), 5'-functionalized non-binding G25A point-mutant of trCLN3 (ABAL-trCLN3 G25A) (2) or no aptamer (−) in presence or absence of UV irradiation. Sample L contained H1838 cell lysate without aptamer. This shows an enrichment of c-Met when using the 5'-functionalized trCLN3 aptamer whereas no band corresponding to c-Met was observed in the bead fraction when using the G25A mutant.

This further underlines the importance of specific binding in combination the UV-induced crosslinking for the enrichment of the target protein from complex mixtures.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of determining a protein in a sample, comprising the steps of:
   (a) providing an aptamer, which is functionalized at the 5'-end with: i) a labeling reagent comprising a photo-activatable crosslinking moiety; ii) a labeling moiety selected from the group consisting of biotin and desthiobiotin, and iii) a linker moiety connecting the labeling reagent to the 5'-end of the aptamer;
   (b) incubating a sample comprising an aptamer target protein with the functionalized aptamer of step (a);
   (c) irradiating the sample with ultraviolet light for cross-linking the aptamer via the photo-activatable crosslinking moiety to the protein, wherein the aptamer is not cleaved by the irradiation; and
   (d) determining the protein via the labeling moiety.

2. The method according to claim 1, wherein the photo-activatable crosslinking moiety is selected from the group comprising aryl azides (phenyl azide), diazirine derivatives such as 3-trifluoromethyl-3-phenyl-diazirine (TPD), and benzophenone derivatives.

3. The method according to claim 1, wherein the linker moiety provides a spacer arm length of about 6 Å to 45 Å between the 5'-end of the aptamer and the crosslinking moiety.

4. The method according to claim 1, wherein the labeling reagent is Sulfosuccinimidyl-2-[6-(biotinamido)-2-(p-azidobenzamido) hexanoamido]ethyl-1,3'-dithiopropionate.

5. The method according to claim 1, wherein the method comprises incubating a biotin-labeled cross-linked aptamer-protein complex formed in step (c) with avidin-, neutravidin-, or streptavidin-coated magnetic beads.

6. The method according to claim 1, wherein step (d) comprises determining a protein in a cell, or in an exosome, or in a circulating microvesicle.

7. The method according to claim 1, wherein step (d) includes determining a protein on the surface of a cell, or an exosome, or a circulating microvesicle.

8. The method according to claim 5, further comprising sorting of the magnetic beads.

9. The method of claim 3, wherein the spacer arm length is about 20 Å to 40 Å.

10. The method of claim 1, wherein the aptamer is functionalized at the 5'-end with a construct consisting of a photo-activatable crosslinking moiety, a labeling moiety selected from the group consisting of biotin and desthiobiotin, and a linker moiety connecting the labeling reagent to the 5'-end of the aptamer.

11. The method of claim 1, wherein the aptamer is functionalized at the 5'-end with a construct consisting of the following structure:

n = 2-10

* * * * *

SEQUENCE LISTING

```
<160> NUMBER OF SEQ ID NOS: 6

<210> SEQ ID NO 1
<211> LENGTH: 35
<212> TYPE: DNA
<213> ORGANISM: Artificial
<220> FEATURE:
<223> OTHER INFORMATION: Aptamer

<400> SEQUENCE: 1
actcgggagg actgcttagg attgcgaacc cgggt                              35

<210> SEQ ID NO 2
<211> LENGTH: 35
<212> TYPE: DNA
<213> ORGANISM: Artificial
<220> FEATURE:
<223> OTHER INFORMATION: Aptamer

<400> SEQUENCE: 2
actcgggagg actgtttagg attgcgaacc cgggt                              35

<210> SEQ ID NO 3
<211> LENGTH: 37
<212> TYPE: DNA
<213> ORGANISM: Artificial
<220> FEATURE:
<223> OTHER INFORMATION: Aptamer

<400> SEQUENCE: 3
ggggcacgtt tatccgtccc tcctagtggc gtgcccc                            37

<210> SEQ ID NO 4
<211> LENGTH: 37
<212> TYPE: DNA
<213> ORGANISM: Artificial
<220> FEATURE:
<223> OTHER INFORMATION: Aptamer

<400> SEQUENCE: 4
```

```
ccagctggct caccgttcgc gctagggctt tccgtcg                              37

<210> SEQ ID NO 5
<211> LENGTH: 40
<212> TYPE: DNA
<213> ORGANISM: Artificial
<220> FEATURE:
<223> OTHER INFORMATION: Aptamer

<400> SEQUENCE: 5
tggatggtag ctcggtcggg gtgggtgggt tggcaagtct                           40

<210> SEQ ID NO 6
<211> LENGTH: 40
<212> TYPE: DNA
<213> ORGANISM: Artificial
<220> FEATURE:
<223> OTHER INFORMATION: Aptamer

<400> SEQUENCE: 6
tggatggtag ctcggtcggg gtggatgggt tggcaagtct                           40
```